US011903636B2

(12) United States Patent
Drochner et al.

(10) Patent No.: US 11,903,636 B2
(45) Date of Patent: Feb. 20, 2024

(54) ENERGY-BASED TISSUE SPECIMEN REMOVAL

(71) Applicant: COVIDIEN LP, Mansfield, MA (US)

(72) Inventors: Thomas E. Drochner, Longmont, CO (US); James D. Allen, IV, Broomfield, CO (US); Dylan R. Kingsley, Broomfield, CO (US); Prakash Manley, Arvada, CO (US); Tony Moua, Broomfield, CO (US); William E. Robinson, Boulder, CO (US); Robert H. Wham, Boulder, CO (US)

(73) Assignee: Covidien LP, Mansfield, MA (US)

(*) Notice: Subject to any disclaimer, the term of this patent is extended or adjusted under 35 U.S.C. 154(b) by 873 days.

(21) Appl. No.: 16/143,787

(22) Filed: Sep. 27, 2018

(65) Prior Publication Data

US 2020/0100835 A1 Apr. 2, 2020

(51) Int. Cl.

| | | |
|---|---|---|
| *A61B 18/14* | (2006.01) | |
| *A61B 17/00* | (2006.01) | |
| *A61B 18/12* | (2006.01) | |
| *A61B 17/34* | (2006.01) | |
| *A61B 18/00* | (2006.01) | |

(52) U.S. Cl.
CPC .... *A61B 18/1482* (2013.01); *A61B 17/00234* (2013.01); *A61B 18/1206* (2013.01); *A61B 17/3423* (2013.01); *A61B 2017/00287* (2013.01); *A61B 2018/00601* (2013.01); *A61B 2018/00875* (2013.01); *A61B 2018/1253* (2013.01)

(58) Field of Classification Search
CPC .......... A61B 18/1482; A61B 17/00234; A61B 18/1206; A61B 17/3423
See application file for complete search history.

(56) References Cited

U.S. PATENT DOCUMENTS

| 5,312,391 A | 5/1994 | Wilk |
|---|---|---|
| 5,403,311 A | 4/1995 | Abele et al. |
| 5,458,598 A | 10/1995 | Feinberg et al. |

(Continued)

FOREIGN PATENT DOCUMENTS

| CN | 104955412 A | 9/2015 |
|---|---|---|
| WO | 0101846 A2 | 1/2001 |
| WO | 2016014589 A1 | 1/2016 |

OTHER PUBLICATIONS

European Examination Report issued in corresponding European Application No. 19 199 944.0 dated Feb. 9, 2021, 4 pages.

(Continued)

*Primary Examiner* — Joseph A Stoklosa
*Assistant Examiner* — Annie L Shoulders
(74) *Attorney, Agent, or Firm* — Carter, DeLuca & Farrell LLP (57) ABSTRACT

A tissue removal system includes an electrosurgical generator including an active electrode port and a return electrode port, an active electrode device configured to connect to the active electrode port, and a return tissue guard configured to connect to the return electrode port. Another tissue removal system includes an electrosurgical generator including an active electrode port and a return electrode port, an active electrode device configured to connect to the active electrode port, and a return specimen bag configured to connect to the return electrode port.

16 Claims, 4 Drawing Sheets

(56) References Cited

U.S. PATENT DOCUMENTS

| | | |
|---|---|---|
| 5,556,397 A | 9/1996 | Long et al. |
| 5,633,578 A | 5/1997 | Eggers et al. |
| 5,814,044 A | 9/1998 | Hooven |
| 5,919,202 A | 7/1999 | Yoon |
| 6,086,583 A | 7/2000 | Ouchi |
| 6,113,596 A | 9/2000 | Hooven et al. |
| 6,379,350 B1 | 4/2002 | Sharkey et al. |
| 6,387,094 B1 | 5/2002 | Eitenmuller |
| 6,440,138 B1 | 8/2002 | Reiley et al. |
| 6,565,560 B1 | 5/2003 | Goble et al. |
| 7,041,101 B2 | 5/2006 | Eggers |
| 7,232,440 B2 | 6/2007 | Dumbauld et al. |
| 7,241,294 B2 | 7/2007 | Reschke |
| 7,303,559 B2 | 12/2007 | Peng et al. |
| 7,510,562 B2 | 3/2009 | Lindsay |
| 7,537,594 B2 | 5/2009 | Sartor |
| 7,588,570 B2 | 9/2009 | Wakikaido et al. |
| 7,935,109 B2 | 5/2011 | Cosmescu |
| 8,267,928 B2 | 9/2012 | Orszulak et al. |
| 8,328,804 B2 | 12/2012 | Heard et al. |
| 8,454,600 B2 | 6/2013 | Huseman |
| 8,636,734 B2 | 1/2014 | Burbank et al. |
| 8,753,341 B2 | 6/2014 | Landry et al. |
| 8,808,287 B2 | 8/2014 | Heard et al. |
| 9,028,490 B2 * | 5/2015 | Heard ............... A61B 18/1485 606/49 |
| 2002/0049442 A1 | 4/2002 | Roberts et al. |
| 2004/0242960 A1 * | 12/2004 | Orban, III ............. A61B 10/06 600/106 |
| 2005/0187547 A1 | 8/2005 | Sugi |
| 2005/0251134 A1 * | 11/2005 | Woloszko ............ A61B 18/149 606/46 |
| 2006/0095027 A1 | 5/2006 | Eggers |
| 2008/0015563 A1 | 1/2008 | Hoey et al. |
| 2009/0254084 A1 | 10/2009 | Naito |
| 2010/0191238 A1 * | 7/2010 | Kornerup ............... A61B 18/14 606/41 |
| 2010/0318080 A1 * | 12/2010 | Keppel ............. A61B 18/1206 606/34 |
| 2013/0178852 A1 | 7/2013 | Allen, IV et al. |
| 2013/0267947 A1 | 10/2013 | Orszulak |
| 2014/0031715 A1 | 1/2014 | Sherar et al. |
| 2016/0022352 A1 | 1/2016 | Johnson et al. |
| 2016/0058495 A1 * | 3/2016 | Twomey ............ A61B 18/1442 606/45 |
| 2016/0157843 A1 * | 6/2016 | Dickson ........... A61B 17/00234 606/47 |
| 2016/0175043 A1 * | 6/2016 | McLawhorn ...... A61B 18/1492 606/49 |
| 2017/0000553 A1 * | 1/2017 | Wiener ............ A61B 18/1233 |
| 2017/0119455 A1 * | 5/2017 | Johnson ................ A61B 18/14 |
| 2017/0224321 A1 * | 8/2017 | Kessler ............. A61B 17/3417 |
| 2017/0231611 A1 * | 8/2017 | Holsten .............. A61B 1/00154 606/114 |

OTHER PUBLICATIONS

Extended European Search Report issued in European Application No. 19199944.0 dated Feb. 20, 2020, 8 pages.

Second Chinese Office Action dated Dec. 5, 2022, issued in corresponding Chinese Appln. No. 201910920508, 9 pages. English translation not available.

First Chinese Office Action dated Jul. 20, 2022 with English translation, issued in corresponding Chinese Appln. No. 201910920508, 18 pages.

* cited by examiner

ENERGY-BASED TISSUE SPECIMEN REMOVAL

BACKGROUND

Technical Field

The present disclosure relates to tissue specimen removal and, more particularly, to electrode configurations facilitating energy-based removal of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity.

During such minimally-invasive surgical procedures, it is common that removal of a cyst, tumor, or other affected tissue is required. In these and other procedures where cancerous tissue is required to be removed, removal of the tissue specimen(s) in an enclosed environment is highly desirable to inhibit seeding of cancer cells. Thus, with respect to breaking down large tissue specimens for removal through minimally-invasive openings, there is the added challenge of doing so within an enclosed environment.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue removal system including an electrosurgical generator including an active electrode port and a return electrode port, an active electrode device configured to connect to the active electrode port, and a return tissue guard configured to connect to the return electrode port.

In an aspect of the present disclosure, the return tissue guard includes an electrically-insulative proximal portion, an at least partially electrically-conductive distal portion, and a cable configured to connect the at least partially electrically-conductive distal portion to the return electrode port.

In another aspect of the present disclosure, the return tissue guard defines an hourglass cross-sectional configuration.

In still another aspect of the present disclosure, an inwardly-facing surface of the return tissue guard is at least partially electrically-conductive and configured to connect to the return electrode port.

In yet another aspect of the present disclosure, the inwardly-facing surface of the return tissue guard includes a first electrically-conductive portion configured to connect to the return electrode port and a second electrically-conductive portion configured to connect to the return electrode port.

In still yet another aspect of the present disclosure, the electrosurgical generator is configured to monitor impedance between the first and second electrically-conductive portions and disable energy output from the active electrode port when the impedance is below a set point.

In another aspect of the present disclosure, the return tissue guard includes a resistor circuit configured to override return electrode monitoring of the electrosurgical generator.

Another tissue removal system provided in accordance with aspects of the present disclosure includes an electrosurgical generator including an active electrode port and a return electrode port, an active electrode device configured to connect to the active electrode port, and a return specimen bag configured to connect to the return electrode port.

In an aspect of the present disclosure, the return specimen bag includes an electrically-insulative outer layer, an at least partially electrically-conductive inner layer, and a cable configured to connect the at least partially electrically-conductive inner layer to the return electrode port.

In another aspect of the present disclosure, the return specimen bag includes a first electrically-conductive portion configured to connect to the return electrode port and a second electrically-conductive portion configured to connect to the return electrode port. The first and second electrically-conductive portions may be joined via an insulative seam.

In still another aspect of the present disclosure, the electrosurgical generator is configured to monitor impedance between the first and second electrically-conductive portions and disable energy output from the active electrode port when the impedance is below a set point.

In yet another aspect of the present disclosure, the return specimen bag includes a resistor circuit configured to override return electrode monitoring of the electrosurgical generator.

A return electrode tenaculum provided in accordance with aspects of the present disclosure includes an end effector assembly. The end effector assembly has a first jaw assembly and a second jaw assembly. The first jaw assembly includes a first electrically-conductive inner jaw and a first electrically-insulative outer jaw disposed about the first electrically-conductive inner jaw. The second jaw assembly includes a second electrically-conductive inner jaw and a second electrically-insulative outer jaw disposed about the second electrically-conductive inner jaw. The first and second electrically-insulative outer jaws are flexible to permit the respective first and second electrically-conductive inner jaws to move from a retracted position within the respective electrically-insulative outer jaws to a protruded position extending at least partially from the respective electrically-insulative outer jaws to contact and grasp tissue therebetween.

In an aspect of the present disclosure, first and second elongated shafts are coupled to the first and second jaw assemblies, respectively, and configured to pivot the first and second jaw assemblies relative to one another between a further spaced-apart position and more-closely approximated position.

In another aspect of the present disclosure, a cable is adapted to connect the first and second electrically-conductive inner jaws to a return electrode port of an electrosurgical generator.

In yet another aspect of the present disclosure, the first and second electrically-conductive inner jaws are electrically isolated from one another. In such aspects, the cable may be configured to connect the first and second electrically-conductive inner jaws to a return electrode port of an electrosurgical generator in electrical isolation from one another.

In still another aspect of the present disclosure, the first and second electrically-conductive inner jaws include tissue-grasping teeth protruding therefrom.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and.

DETAILED DESCRIPTION

The present disclosure provides tissue removal systems including electrode configurations facilitating energy-based removal of a tissue specimen from an internal body cavity while maintaining the tissue specimen in an enclosed environment during break down and removal from the internal body cavity.

Figure 1:
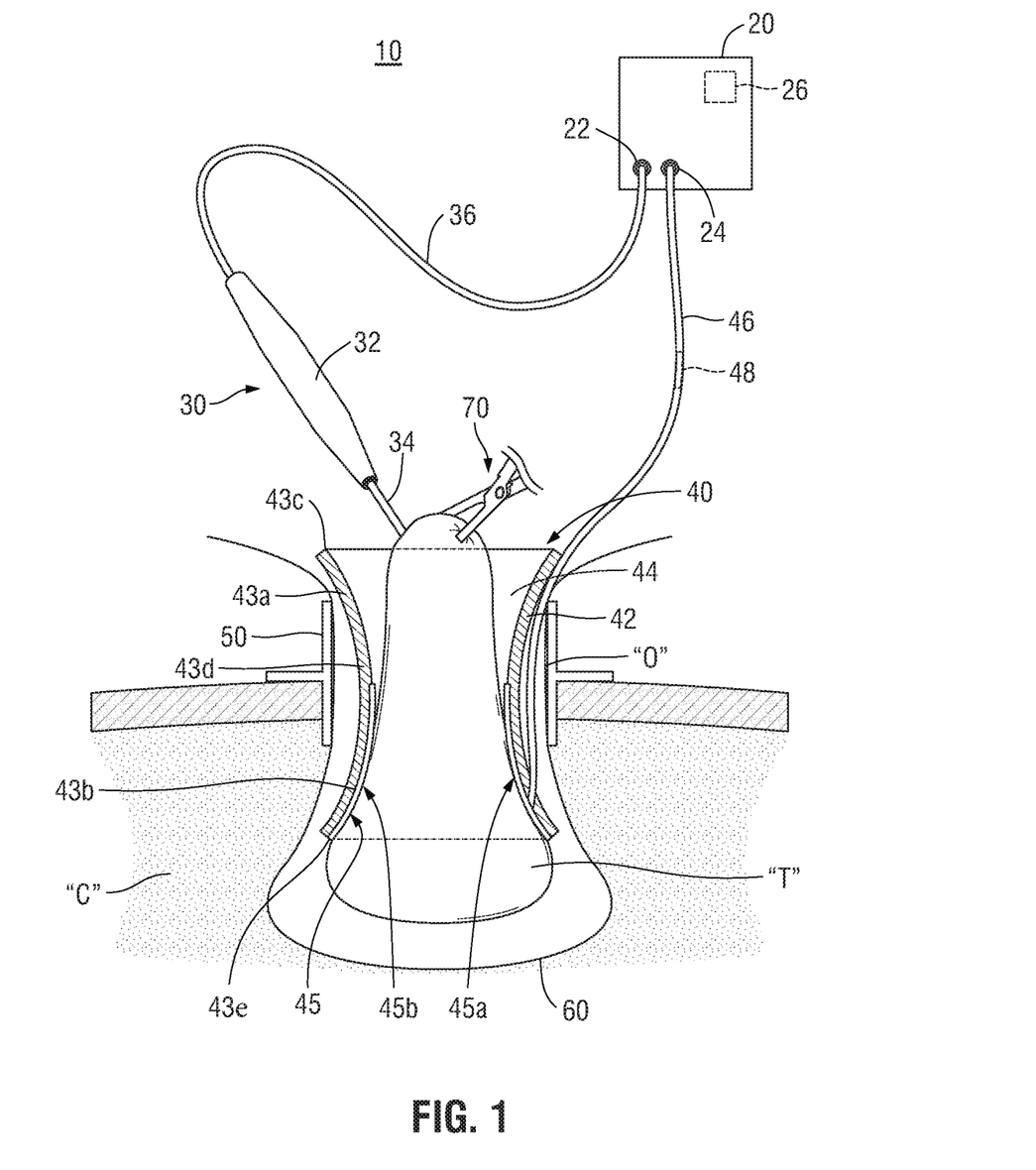
FIG. 1 is a transverse, cross-sectional view illustrating a tissue specimen removal system in accordance with the present disclosure in use removing a tissue specimen from an internal body cavity.

Turning to FIG. 1, a tissue removal system provided in accordance with the present disclosure is shown generally identified by reference numeral 10. System 10 includes an electrosurgical generator 20, an active electrode device, e.g., a monopolar surgical pencil 30, and a return electrode device, e.g., a return tissue guard 40. System 10 may further include an access port 50 configured for positioning within an opening "O" in tissue providing access to an internal body cavity "C," a specimen bag 60 configured to receive and retain a tissue specimen "T" therein to enable breakdown and removal of the tissue specimen "T" while the tissue specimen "T" remains isolated from the internal body cavity "C," and/or a tenaculum 70 to facilitate manipulation and extraction of the tissue specimen "T."

Electrosurgical generator 20 is configured to enable use in a monopolar mode and, thus, includes an active electrode port 22 and a return electrode port 24. Electrosurgical generator 20 may incorporate a Return Electrode Monitoring (REM) module 26 coupled to return electrode port 24 and configured to measure the impedance of the return electrode (which will vary based upon the contact area between tissue and the return electrode) and inhibit the output of energy via active electrode port 22 if the impedance drops below a set point (thus indicating insufficient contact area between tissue and the return electrode).

The active electrode device is configured as a monopolar surgical pencil 30, although other suitable active electrode devices are also contemplated. Monopolar surgical pencil 30 includes a handle 32, a probe 34 extending distally from handle 32, and a cable 36 extending proximally from handle 32. Handle 32 is configured to enable a user to grasp and manipulate monopolar surgical pencil 30 and may include one or more controls (not shown), e.g., switches, buttons, etc., to enable a user to control the application of energy from active electrode probe 34 to tissue. Probe 34 is at least partially formed from an electrically-conductive material to supply energy to tissue in contact therewith. Cable 36 terminates in a plug configured to engage active electrode port 22 of electrosurgical generator 20 to enable the supply of energy from electrosurgical generator 20 to probe 34, for application from probe 34 to tissue.

The return electrode device is configured as a return tissue guard 40 and functions to both protect tissue, e.g., inhibiting cutting or puncturing of the specimen bag 60, and serve as a return electrode pathway back to electrosurgical generator 20. Return tissue guard 40 includes a body 42 and a cable 46 coupled to body 42. Body 42 includes a proximal portion 43a and a distal portion 43b. Proximal portion 43a extends from a proximal end 43c of body 42 to an intermediate waist 43d of body 42, while distal portion 43b extends from a distal end 43e of body to intermediate waist 43d of body 42. Body 42 defines a generally hourglass cross-sectional configuration wherein proximal and distal ends 43c, 43e, respectively, of body 42 define relatively larger diameters (similar or different) whereas intermediate waist 43d defines a relatively narrower diameter. Other suitable configurations are also contemplated. Proximal and distal ends 43c, 43e of body 42 may define similar or different diameters and/or proximal and distal portions 43a, 43b may define similar or different lengths. A passageway 44 extends through body 42 from the proximal end 43c to the distal end 43e thereof to permit passage of instrumentation, tissue, etc. through return tissue guard 50.

Proximal portion 43a of body 42 of return tissue guard 40 is electrically-insulative while at least a portion of the inwardly-facing surface 45 of distal portion 43b of body 42 of return tissue guard 40 is electrically-conductive. Body 42 may be formed from a cut and/or puncture-resistant electrically-insulative material and include an electrically-conductive material attached, coated, or otherwise disposed on distal portion 43b thereof to define the electrically-conductive inwardly-facing surface 45 of distal portion 43b. Alternatively, body 42 may be formed from a cut and/or puncture-resistant electrically-conductive material and include an electrically-insulative coating disposed on all but the electrically-conductive inwardly-facing surface 45 of distal portion 43b. Other suitable configurations are also contemplated.

In embodiments, inwardly-facing surface 45 of distal portion 43b of body 42 includes first and second electrically-conductive inwardly-facing surface portions 45a, 45b electrically isolated from one another. In such embodiments, the first surface portion 45a may be disposed on a first side portion, e.g., a first half, of body 42 while the second surface portion 45b is disposed on a second, opposing side portion, e.g., a second half, of body 42.

Cable 46 is electrically coupled with electrically-conductive inwardly-facing surface 45 of distal portion 43b of body 42 and extends to a plug configured to engage return electrode port 24 of electrosurgical generator 20 to complete the circuit back to electrosurgical generator 20 from energy supplied to tissue from electrosurgical generator 20 via probe 34. In embodiments where first and second electrically-conductive inwardly-facing surface portions 45a, 45b are provided, cable 46 may include first and second leads (not shown) electrically-isolated from one another and coupled to the respective first and second surface portions 45a, 45b.

In use, with the tissue specimen "T" disposed within specimen bag 60 within the internal body cavity "C," tenaculum 70 may be utilized to grasp and pull a portion of the tissue specimen "T" at least partially through passageway 44 of return tissue guard 40 such that the portion of the tissue specimen "T" extends through intermediate waist 43d of body 42 of return tissue guard 40 and into or through proximal portion 43a of body 42 of return tissue guard 40. As the tissue specimen "T" is pulled in this manner, a portion of the tissue specimen "T" contacts the electrically-conductive inwardly-facing surface 45 of distal portion 43b of body 42. Contact between the tissue specimen "T" and electrically-conductive inwardly-facing surface 45 is facilitated due to the hourglass cross-sectional configuration of return tissue guard 40.

With the tissue specimen "T" extending into or through proximal portion 43a of body 42 of return tissue guard 40 and in contact with electrically-conductive inwardly-facing surface 45 of distal portion 43b of body 42 of return tissue guard 40, monopolar surgical pencil 30 may be maneuvered into position such that probe 34 thereof contacts the tissue specimen "T" and, thereafter, may be activated to deliver energy to the tissue specimen "T" to cut the tissue specimen "T" into smaller pieces to facilitate removal from the internal body cavity "C." The energy supplied to the tissue specimen "T" from probe 34 of monopolar surgical pencil 30 is returned to electrosurgical generator 20 via the electrically-conductive inwardly-facing surface 45 of return tissue guard 40 which, as noted above, is disposed in contact with the tissue specimen "T" to complete the electrical circuit.

In embodiments where generator 20 includes REM module 26 and REM is activated, cable 46 may include a resistor circuit 48 configured to provide the requisite impedance to REM module 26 such that REM module 26 does not inhibit the output of energy via active electrode port 22. Alternatively, in embodiments where first and second electrically-conductive inwardly-facing surface portions 45a, 45b are provided, REM module 26 may measure the impedance therebetween and inhibit the output of energy via active electrode port 22 if the impedance drops below the set point.

Figure 2:
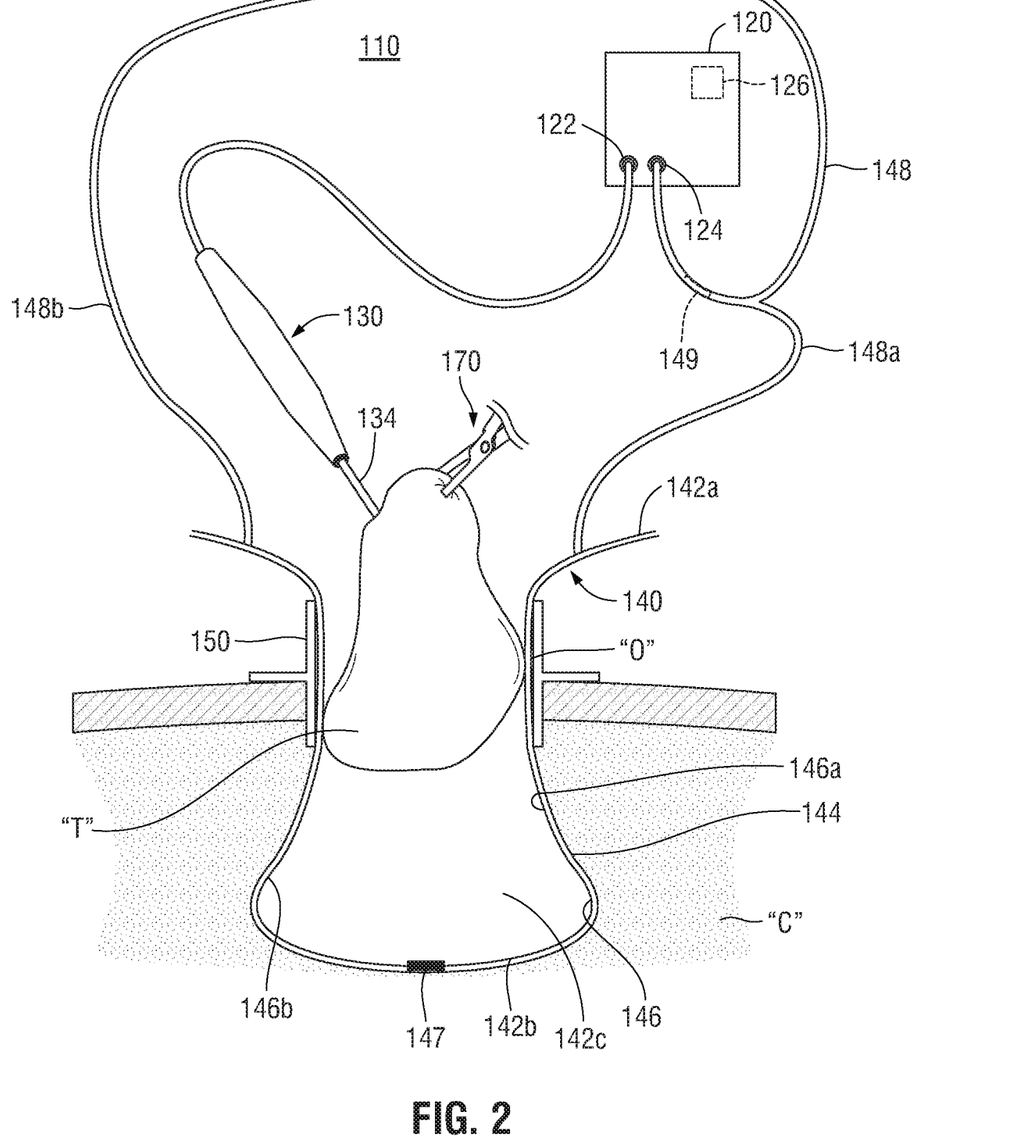
FIG. 2 is a transverse, cross-sectional view illustrating another tissue specimen removal system in accordance with the present disclosure in use removing a tissue specimen from an internal body cavity.

Referring to FIG. 2, another tissue removal system provided in accordance with the present disclosure is shown generally identified by reference numeral 110. System 110 includes an electrosurgical generator 120, an active electrode device, e.g., a monopolar surgical pencil 130, and a return electrode device, e.g., a return specimen bag 140. System 110 may further include an access port 150 configured for positioning within an opening "O" in tissue providing access to an internal body cavity "C." As return specimen bag 140 is provided, a separate specimen bag is not required; rather, return specimen bag 140 is configured to receive and retain a tissue specimen "T" therein to enable breakdown and removal of the tissue specimen "T" while the tissue specimen "T" remains isolated from the remainder of the internal body cavity "C." System 110 may further include a tenaculum 170 to facilitate manipulation and extraction of the tissue specimen "T."

Electrosurgical generator 120, monopolar surgical pencil 130, and tenaculum 170 are similar to electrosurgical generator 20, monopolar surgical pencil 30, and tenaculum 70 of system 10 (see FIG. 1) and, thus, are not described in detail hereinbelow to avoid unnecessary repetition.

Return specimen bag 140 functions to both isolate the tissue specimen "T" from the internal body cavity "C" tissue and serve as a return electrode pathway back to electrosurgical generator 120. Return specimen bag 140 includes an open end 142a and a closed end 142b and defines an internal area 142c. Return specimen bag 140 is formed from an electrically-insulative outer layer 144 and an at least partially electrically-conductive inner layer 146. Electrically-insulative outer layer 144 may be formed from, for example, nylon, urethane, ripstop nylon, latex, or other suitable material that provides an electrically-insulative outer layer 144. At least partially electrically-conductive inner layer 146 may be formed from, for example, an at least partially-conductive fabric, an at least partially-conductive mesh, etc., and may be joined to electrically-insulative outer layer 144 via an adhesive, mechanical engagement, etc. or may be freely seated within electrically-insulative outer layer 144.

In embodiments, electrically-conductive inner layer 146 includes first and second electrically-conductive portions 146a, 146b electrically isolated from one another, e.g., via an insulated seam 147. In such embodiments, the first portion 146a may be disposed on a first side portion, e.g., a first half, of electrically-conductive inner layer 146 while the second portion 146b is disposed on a second, opposing side portion, e.g., a second half, of electrically-conductive inner layer 146. As an alternative to first and second halves, multiple first portions 146a and second portions 146b may be provided and arranged in alternating fashion annularly about inner layer 146, e.g., similarly as the different colored sections of a beach ball.

Return specimen bag 140 further includes a cable 148 electrically coupled with electrically-conductive inner layer 146 and extending to a plug configured to engage return electrode port 124 of electrosurgical generator 120 to complete the circuit back to electrosurgical generator 120 from energy supplied to tissue from electrosurgical generator 120 via probe 134 of monopolar surgical pencil 130. In embodiments where first and second electrically-conductive portions 146a, 146b of inner layer 146 are provided, cable 148 may include first and second cable potions 148a, 148b electrically-isolated from one another and coupled to the respective first and second portions 146a, 146b.

In use, with the tissue specimen "T" disposed within return specimen bag 140 within the internal body cavity "C," tenaculum 170 may be utilized to grasp and pull a portion of the tissue specimen "T" at least partially through the opening "O" in tissue such that a portion of the tissue specimen "T" is disposed in contact with return specimen bag 140.

With the tissue specimen "T" disposed in contact with return specimen bag 140, monopolar surgical pencil 130 may be maneuvered into position such that probe 134 thereof contacts the tissue specimen "T" and, thereafter, may be activated to deliver energy to the tissue specimen "T" to cut the tissue specimen "T" into smaller pieces to facilitate removal from the internal body cavity "C." The energy supplied to the tissue specimen "T" from probe 134 of monopolar surgical pencil 130 is returned to electrosurgical generator 120 via the at least partially electrically-conductive inner layer 146 of return specimen bag 140 which, as noted above, is disposed in contact with the tissue specimen "T" to complete the electrical circuit.

In embodiments where generator 120 includes REM module 126 and REM is activated, cable 148 may include a resistor circuit 149 configured to provide the requisite impedance to REM module 126 such that REM module 126 does not inhibit the output of energy via active electrode port 122. Alternatively, in embodiments where first and second electrically-conductive portions 146a, 146b of inner layer 146 are provided, REM module 126 may measure the impedance therebetween and inhibit the output of energy via active electrode port 122 if the impedance drops below the set point.

Figure 3:
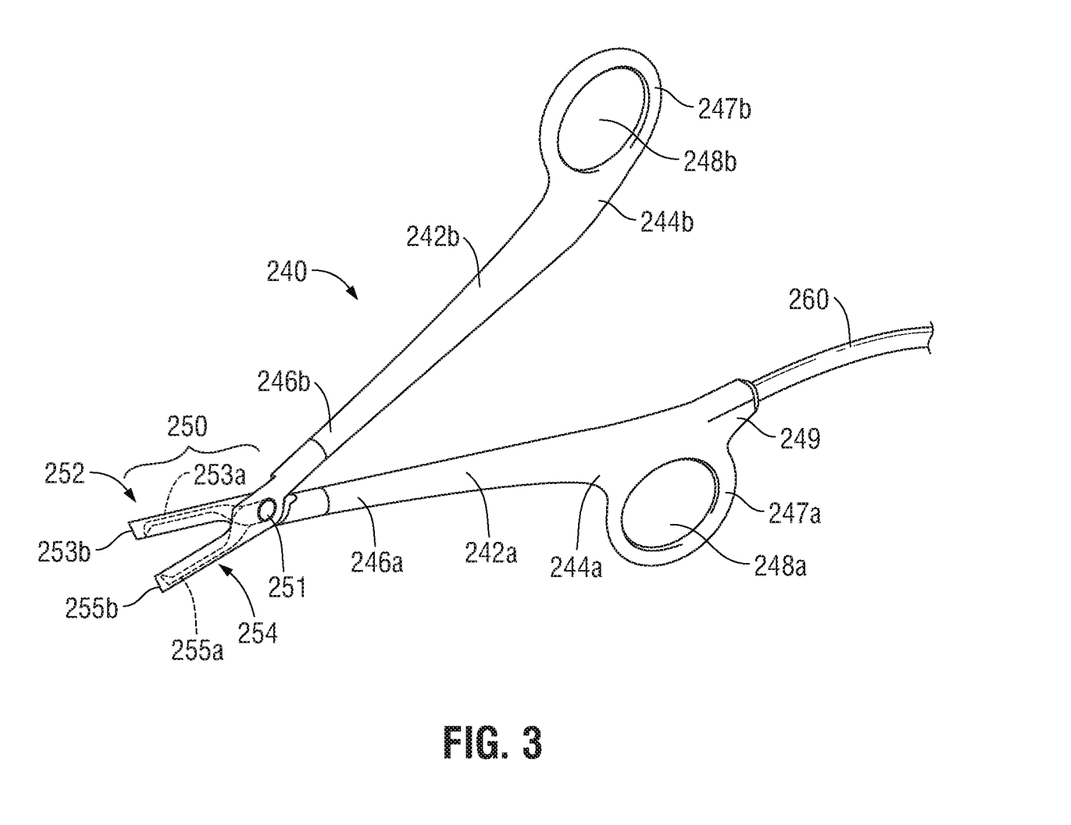
FIG. 3 is a perspective view of a tissue removal device provided in accordance with the present disclosure.

Turning to FIGS. 3-5B, and initially to FIG. 3, a return electrode device configured as a return electrode tenaculum is shown generally identified by reference numeral 240. Return electrode tenaculum 240 may be part of a tissue removal system including, for example, an electrosurgical generator, an active electrode device, e.g., a monopolar surgical pencil, an access port, and/or a specimen bag, similarly as detailed above with respect to system 10 (FIG. 1).

Return electrode tenaculum 240 includes two elongated shaft 242a, 242b, each having a proximal end 244a, 244b, and a distal end 246a, 246b, respectively. An end effector assembly 250 including first and second jaw assemblies 252, 254 extends from distal ends 246a, 246b of elongated shaft 242a, 242b, respectively. Each elongated shaft 242a, 242b includes a handle 247a, 247b disposed at the proximal end 244a, 244b thereof. Each handle 247a, 247b defines a finger hole 248a, 248b therethrough for receiving a finger of the user. As can be appreciated, finger holes 248a, 248b facilitate movement of elongated shafts 242a, 242b relative to one another to, in turn, pivot jaw assemblies 252, 254 of end effector assembly 250 about pivot 251 and relative to one another between a further spaced-apart position and a more-closely approximated position.

One of the elongated shafts, e.g., elongated shaft 242a, includes a proximal shaft connector 249 supporting a cable 260 configured to connect return electrode tenaculum 240 to a return electrode port of an electrosurgical generator similar to electrosurgical generator 20 (FIG. 1).

Figure 4:
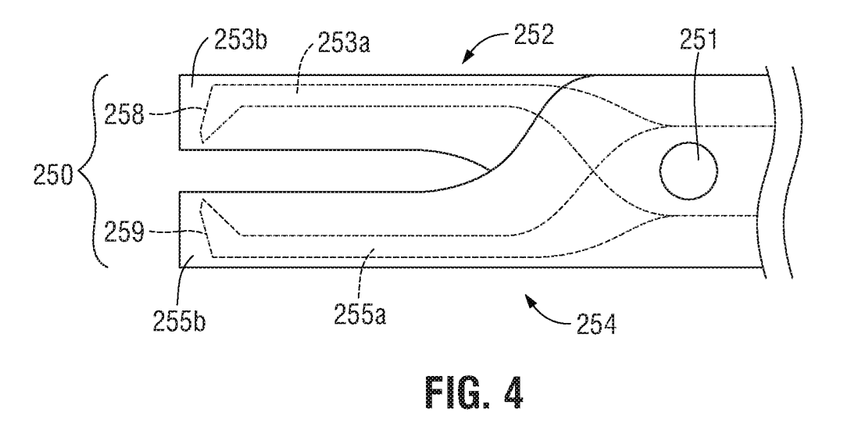
FIG. 4 is a side view of an end effector assembly of the tissue removal device of FIG. 3.

With additional reference to FIGS. 4A and 4B, end effector assembly 250 of return electrode tenaculum 240, as noted above, includes first and second jaw assemblies 252, 254 attached to respective distal ends 246a, 246b of elongated shafts 242a, 242b and pivotably coupled to one another about a pivot 251. Each jaw assembly 252, 254 include an inner jaw 253a, 255a and an outer jaw 253b, 255b, respectively. Inner jaws 253a, 255a are at least partially formed from an electrically-conductive material, are rigidly coupled to elongated shafts 242a, 242b, respectively, and are pivotably coupled to one another about pivot 251. Inner jaws 253a, 255a are electrically coupled to cable 260 and may be coupled to the same electrical lead of cable 260 or first and second electrical leads of cable 260 that are electrically-isolated from one another. In embodiments, inner jaws 253a, 355a include tissue-grasping teeth 258, 259 at the distal ends thereof to facilitate grasping tissue therewith.

Outer jaws 253b, 255b are disposed about distal ends 246a, 246b of elongated shafts 242a, 242b and inner jaws 253a, 255a, respectively, and are formed from a flexible, electrically-insulative material to enable the portions of outer jaws 253b, 255b disposed about inner jaws 253a, 255a to flex relative to the portions of outer jaws 253b, 255b disposed about elongated shafts 242a, 242b. Outer jaws 253b, 255b also define slots (not shown) on the opposed faces thereof to enable inner jaws 253a, 255a to extend from outer jaws 253b, 255b upon flexion of outer jaws 253b, 255b, as detailed below.

Figure 5A:
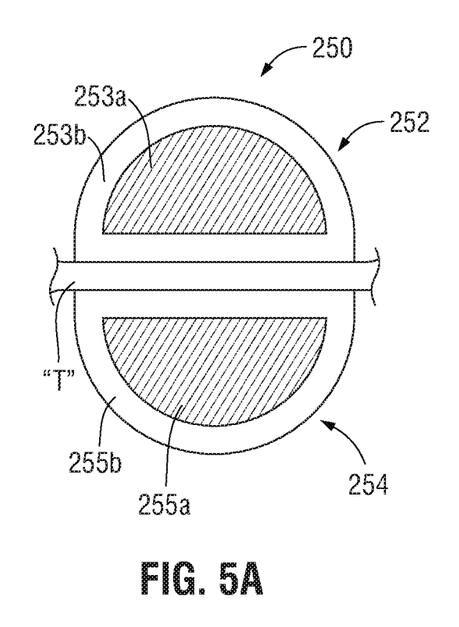
FIG. 5A is a transverse, cross-sectional view of the end effector assembly of the tissue removal device of FIG. 3 grasping tissue therebetween with inner jaws thereof disposed in a retracted position.
Figure 5B:
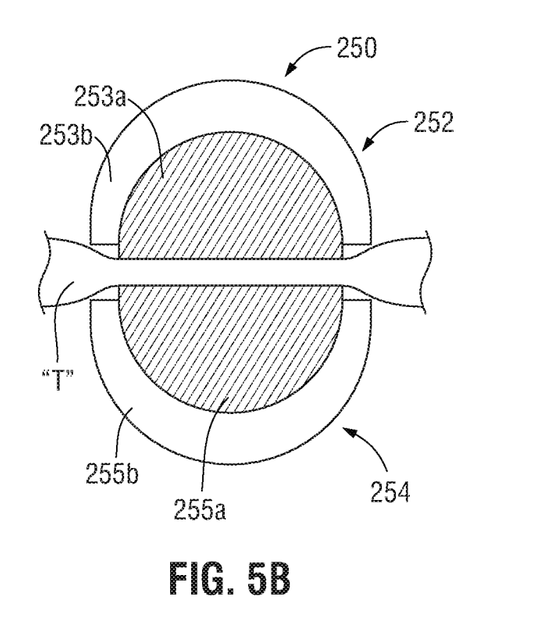
FIG. 5B is a transverse, cross-sectional view of the end effector assembly of the tissue removal device of FIG. 3 grasping tissue therebetween with inner jaws thereof disposed in a protruded position.

Referring to FIGS. 5A and 5B, in conjunction with FIGS. 3 and 4, in use, return electrode tenaculum 240 is manipulated such that the portion of the tissue specimen "T" to be grasped is disposed between jaw assemblies 252, 254. Thereafter, elongated shafts 242a, 242b are pivoted towards one another, e.g., using handles 247a, 247b, such that jaw assemblies 252, 254 are pivoted about pivot 251 from the further spaced-apart position towards the more-closely approximated position to grasp the tissue specimen "T" therebetween.

As illustrated in FIG. 5A, although tissue is grasped between jaw assemblies 252, 254, tissue is only grasped between electrically-insulative outer jaws 253b, 255b thereof as inner jaws 253a, 255a remain disposed within outer jaws 253b, 255b. Thus, inner jaws 253a, 255a are not in contact with the tissue specimen "T."

As illustrated in FIG. 5B, upon further pivoting of elongated shafts 242a, 242b towards one another, outer jaws 253b, 255b are urged against the tissue specimen "T" and, as a result, the portions of outer jaws 253b, 255b disposed about inner jaws 253a, 255a are flexed apart from one another such that inner jaws 253a, 255b protrude from outer jaws 253b, 255b and directly contact and grasp the tissue specimen "T."

With inner jaws 253a, 255b directly contacting and grasping the tissue specimen "T," a monopolar surgical pencil or other active electrode device may be moved into contact with the tissue specimen "T" and activated to deliver energy to the tissue specimen "T" to cut the tissue specimen "T" into smaller pieces to facilitate removal from an internal body cavity. The energy supplied to the tissue specimen "T" from the monopolar surgical pencil is returned to the electrosurgical generator via the electrically-conductive inner jaws 253a, 255b of return electrode tenaculum 240 which, as noted above, are disposed in contact with and grasping the tissue specimen "T" to complete the electrical circuit.

By allowing electrically-conductive inner jaws 253a, 255b to contact and grasp tissue (and, thus, complete the electrical circuit) only when end effector assembly 250 of return electrode tenaculum 240 is sufficiently grasping the tissue specimen "T," appropriate contact between return electrode tenaculum 240 and the tissue specimen "T" is ensured.

In embodiments where the electrosurgical generator used with return electrode tenaculum 240 includes a REM module and REM is activated, cable 260 (or another portion of return electrode tenaculum 240) may include a resistor circuit configured to provide the requisite impedance to the REM module such that the REM module does not inhibit the output of energy from the electrosurgical generator. Alternatively, in embodiments where isolated electrically-conductive inner jaws 253a, 255b are provided, the REM module may measure the impedance therebetween and inhibit the output of energy if the impedance drops below the set point.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue removal system, comprising:
an electrosurgical generator including an active electrode port and a return electrode port;
an active electrode device configured to connect to the active electrode port; and
a tubular return tissue guard configured to connect to the return electrode port, the tubular return tissue guard having a proximal end defining a proximal opening, a distal end defining a distal opening, and an intermediate waist portion between the proximal end and the distal end, wherein a diameter of the intermediate waist portion is less than a diameter of the proximal opening and a diameter of the distal opening, and wherein an inwardly-facing surface of the tubular return tissue guard defines a tubular channel and includes a first electrically-conductive portion and a second electrically-conductive portion, the first and second electrically-conductive portions disposed on the inwardly-facing surface of the tubular return tissue guard and extending from the intermediate waist portion to the distal end of the tubular return tissue guard, the first electrically-conductive portion configured to connect to the return electrode port and the second electrically-conductive portion electrically isolated from the first electrically-conductive portion and configured to connect to the return electrode port.

2. The tissue removal system according to claim 1, wherein the tubular return tissue guard includes an electrically-insulative proximal portion, an at least partially electrically-conductive distal portion, and a cable configured to connect the at least partially electrically-conductive distal portion to the return electrode port.

3. The tissue removal system according to claim 1, wherein the tubular return tissue guard defines an hourglass cross-sectional configuration.

4. The tissue removal system according to claim 1, wherein the electrosurgical generator is configured to monitor impedance between the first and second electrically-conductive portions and disable energy output from the active electrode port when the impedance is below a set point.

5. The tissue removal system according to claim 1, wherein the tubular return tissue guard includes a resistor circuit configured to override return electrode monitoring of the electrosurgical generator.

6. The tissue removal system according to claim 1, wherein the active electrode device is a monopolar electrosurgical pencil.

7. A tissue removal system, comprising:
an active electrode device configured to connect to an active electrode port of an electrosurgical generator; and
a tubular return tissue guard configured to connect to a return electrode port of the electrosurgical generator, the tubular return tissue guard having a proximal end defining a proximal opening, a distal end defining a distal opening, and an intermediate waist portion between the proximal end and the distal end, wherein a diameter of the intermediate waist portion is less than a diameter of the proximal opening and a diameter of the distal opening, and wherein an inwardly-facing surface of the tubular return tissue guard defines a tubular channel and includes a first electrically-conductive portion and a second electrically-conductive portion, the first and second electrically-conductive portions disposed on the inwardly-facing surface of the tubular return tissue guard and extending from the intermediate waist portion to the distal end of the tubular return tissue guard, the first electrically-conductive portion configured to connect to the return electrode port and the second electrically-conductive portion electrically isolated from the first electrically-conductive portion and configured to connect to the return electrode port,
wherein the tubular return tissue guard is configured for positioning within an opening in tissue such that an outwardly-facing surface of the tubular return tissue guard abuts the tissue when the tubular return tissue guard is positioned within the opening in tissue, and
wherein the active electrode device is configured for insertion through the tubular return tissue guard into an internal surgical site.

8. The tissue removal system according to claim 7, wherein the tubular return tissue guard includes an electrically-insulative proximal portion, an at least partially electrically-conductive distal portion, and a cable configured to connect the at least partially electrically-conductive distal portion to the return electrode port of the electrosurgical generator.

9. The tissue removal system according to claim 7, wherein the tubular return tissue guard defines an hourglass cross-sectional configuration.

10. The tissue removal system according to claim 7, wherein the tubular return tissue guard includes a resistor circuit operably coupled thereto.

11. The tissue removal system according to claim 7, wherein the active electrode device is a monopolar electrosurgical pencil.

12. A tissue removal system, comprising:
a monopolar electrosurgical pencil configured to connect to an active monopolar port of an electrosurgical generator, the monopolar electrosurgical pencil configured to apply electrosurgical energy received from the electrosurgical generator to tissue to cut tissue; and
a tubular tissue guard configured for positioning within an opening in tissue, the tubular tissue guard including an inner surface defining a tubular passageway therethrough, the tubular tissue guard having a proximal end defining a proximal opening, a distal end defining a distal opening, and an intermediate waist portion between the proximal end and the distal end, wherein a diameter of the intermediate waist portion is less than a diameter of the proximal opening and a diameter of the distal opening, the tubular tissue guard including a first electrically-conductive portion and a second electrically-conductive portion, the first and second electrically-conductive portions disposed on the inner surface of the tubular tissue guard and extending from the intermediate waist portion to the distal end of the tubular tissue guard, the first electrically-conductive portion electrically isolated from the second electrically-conductive portion, the first and second electrically-conductive portions configured to connect to a return monopolar port of the electrosurgical generator to return electrosurgical energy from tissue to the electrosurgical generator.

13. The tissue removal system according to claim 12, further comprising the electrosurgical generator including the active monopolar port and the return monopolar port.

14. The tissue removal system according to claim 12, wherein a proximal portion of the inner surface of the tubular tissue guard is electrically-insulative and wherein a distal portion of the inner surface of the tubular tissue guard includes the first and second electrically-conductive portions.

15. The tissue removal system according to claim 12, wherein the tubular tissue guard defines an hourglass cross-sectional configuration.

16. The tissue removal system according to claim 12, wherein the tubular tissue guard includes a resistor circuit operably coupled thereto.

\* \* \* \* \*